US00PP26311P2

(12) United States Plant Patent
Sproul

(10) Patent No.: US PP26,311 P2
(45) Date of Patent: Jan. 19, 2016

(54) FLORIBUNDA ROSE PLANT NAMED 'SPROCHOOSE'

(50) Latin Name: *Rosa hybrida*
Varietal Denomination: SPRochoose

(71) Applicant: James A. Sproul, Bakersfield, CA (US)

(72) Inventor: James A. Sproul, Bakersfield, CA (US)

( * ) Notice: Subject to any disclaimer, the term of this patent is extended or adjusted under 35 U.S.C. 154(b) by 325 days.

(21) Appl. No.: 13/998,081

(22) Filed: Sep. 30, 2013

(51) Int. Cl.
*A01H 5/02* (2006.01)

(52) U.S. Cl.
USPC ..... Plt./143

(58) Field of Classification Search
USPC ..... Plt./143
CPC ..... A01H 5/0222; A01H 5/0216; A01H 5/02; A01H 5/00
See application file for complete search history.

*Primary Examiner* — Kent L Bell

(57) ABSTRACT

'SPRochoose' is a new and distinct variety of rose plant of the floribunda class with flowers of a striking pink blend in an exhibition, hybrid tea form. These flowers are borne initially in clusters that become the center of large sprays of 10 to 40 blooms or more. It has a vigorous and continuous blooming habit, with very good resistance to downy mildew and other rose diseases.

2 Drawing Sheets

Genus and species: *Rosa hybrida.*

Varietal denomination: This new cultivar has the varietal denomination of 'SPRochoose'.

BACKGROUND OF THE INVENTION

This new and distinct variety of hardy, bush type rose plant of the floribunda class was developed by me, James A. Sproul, under conditions of careful and controlled observation, at my nursery in Bakersfield, Calif. It is the result of crossing two seedlings I had previously developed in my breeding program:

'Pearl Sanford', a miniature rose, not patented or registered, as the seed parent.

The pollen parent was an unnamed, unregistered and unintroduced floribunda.

The objective in making the cross that led to 'SPRochoose' was to produce an attractive and highly disease resistant rose plant with classic, hybrid tea formed flowers. To meet this objective, the parents were chosen for their disease resistance and attractive hybrid tea formed flowers. The objective was substantially achieved in this new rose variety with its fully double, exhibition, hybrid tea form blooms on a plant since proven to have above average resistance to disease by testing in several areas across the United States.

This current plant may be compared with its parents, as shown here in Table 1.

TABLE 1

| | CURRENT PLANT: 'SPROCHOOSE' | SEED PARENT: 'PEARL SANFORD' | POLLEN PARENT: SEEDLING |
|---|---|---|---|
| CLASS | Floribunda | Miniature | Floribunda |
| BLOOM COLOR | Creamy White and Pink Blend | White and Pink Blend | Deep Coral Pink |
| FLOWER BLOOM SIZE, | Fully Double average: 3 inches in MA | Double average: 1½ inches | Double average: 3 inches |

TABLE 1-continued

| | CURRENT PLANT: 'SPROCHOOSE' | SEED PARENT: 'PEARL SANFORD' | POLLEN PARENT: SEEDLING |
|---|---|---|---|
| EXPANDED | 3½ inches in CA | (only grown in CA) | (only grown in CA) |
| BLOOM HABIT | Tight clusters develop into large sprays throughout the season | Small clusters throughout the season | Small clusters; rapid repeat throughout the season |
| FRAGRANCE | Slight to moderate | Mild | Slight |
| PLANT HABIT | Upright; 3 to 3½ feet tall and wide | 16 to 20 inches tall and well rounded | Upright, to 3 feet tall. |
| FOLIAGE | Glossy to semi-glossy | Semi-glossy | Semi-glossy |

Subsequent to the origination of the cultivar, it was successfully reproduced by rooting cuttings in Bakersfield and Arroyo Grande, Calif., and by budding onto 'Dr. Huey' (not patented) rootstock in Wasco, Calif. Flowers of these reproductions were noted to run true in all aspects.

SUMMARY OF THE INVENTION

This present invention relates to a new and distinct cultivar of hardy, bush type rose plant of the floribunda class that has several features distinguishing it from other presently available roses, of which I am aware. Among these characteristics is the unique combination of the following:

flowers borne initially in tight clusters that became the center of large sprays of buds and blooms of 10 to 16 or more on young plants, and up to 40 or more on mature plants;

multiplicity of colors, and shades of those colors, in each flower;

their fully double, hybrid tea formed flowers;

the length of time the flowers last on the plant;

its vigorous growth and continuous blooming habit;

its upright plant habit;

its dark green, semi-glossy foliage;

the distinctive red veins in the young foliage;

its above average resistance to powdery mildew and black spot;

its ability to grow well in containers and in the ground;

its ability to root easily from cuttings and to take readily when budded.

BRIEF DESCRIPTION OF THE DRAWINGS

The first page of the accompanying illustrations has color pictures taken on Jun. 21, 2012, showing three different views of integral parts of the plants as grown in Ipswich, Mass., receiving full sun for only five to six hours in the middle of the day.

Image #1-1 is a view showing the plant structure of a flowering cane, at near actual size, with straight and strong flowering stems that developed from the nodes below the original cluster, which in this instance had been cut off.

Image #1-2 is more of a side view of the early stages of a spray of flowers that opened as a pink and creamy white blend, and showing points of origination of flowering stems forming the cluster at the top of this spray, a view of the peduncles and accompanying foliage.

Picture, #1-3, is the top view of a typical cluster at the beginning stages of a developing spray, showing buds, opening blooms and a fading bloom of flowers that initially opened predominately creamy white. On the right side of this cluster, a second and smaller cluster can be seen as part of the developing spray, originating from a node immediately below this first cluster.

The color pictures on the second page show flowers and plants as grown in full sun in Bakersfield, Calif.

Image #2-1, taken on Jun. 25, 2012, is of a mature plant growing in full sun in the ground.

Image #2-2, taken May 1, 2010, is a single bloom at exhibition stage.

Image #2-3, taken on Jun. 25, 2012, shows the typical stage of the central flower in a spray as the buds immediately beneath it were just starting to unfurl.

Colors are depicted as nearly correct as is possible in a color illustration of this character.

BOTANICAL DESCRIPTION OF THE PLANT

Following is a detailed description pertaining specifically to this new and distinct variety of rose plant as observed at around three to five years of age, growing on 'Dr. Huey' root stock in 15 and 20 inch nursery containers, in Ipswich, Mass. Occasional information is from plants grown in containers or in the ground in Bakersfield, Calif., and is so noted. Phenotypic expression can be somewhat variable particularly in relation to differing cultural conditions. Color references are made using The Royal Horticultural Society (London, England) Colour Chart except where common terms of color are used.

FLOWERS

Blooming habit: Continual bloom on mature plants, new flowers opened before older blooms faded, and new buds continually developed.

Borne: Flowers began in clusters of three to six blooms, with a central bud opening and maturing well ahead of the others in the cluster. As the buds in this clusters grew and matured, additional flowering stems developed from the nodes progressively below the clusters. These grew up quickly and, on mature plants, developed clusters of their own, each with 2 to 6 blooms that opened quickly, to constitute a large spray of blooms in all stages. Young plants may have only a single bloom on most of these additional flowering stems.

Bud:

*Form.*—Was ovoid, truncated at the base and with a cuspidate apex.

*Size.*—Before the sepals divided the widths of the centermost buds in each cluster varied from $^{17}/_{32}$ inch to $^{19}/_{32}$ inch, but were most often $^{18}/_{32}$ inch. Lengths of those buds varied from $^{23}/_{32}$ to $^{25}/_{32}$ inch. (1) The widths of the second highest buds in a cluster were most often $^{15}/_{32}$ inch but were measured up to as much as $^{19}/_{32}$ inch; lengths of each bud were $^{1}/_{32}$ to $^{3}/_{32}$ inch greater than their widths. (2) The widths of the third highest buds in the clusters were measured from $^{13}/_{32}$ to $^{18}/_{32}$ inch; lengths were about the same as the width, being not more than $^{1}/_{32}$ inch greater or smaller. (3) When present, the widths of the fourth highest buds in a cluster measured from $^{15}/_{32}$ to $^{16}/_{32}$ inch; lengths were about the same as their widths, being not more than $^{1}/_{32}$ inch less or $^{2}/_{32}$ inch greater. (4) When an additional bud was present in a cluster, it was generally the same size as the fourth highest bud in that cluster.

*Color when sepals first divide.*—Sometimes different color combinations were noted on same bud. The first colors visible on some buds were a light Chartreuse Green, near 1C, surrounding a basal area of a darker yellow green, near 145B, while other petals on the same bud were a very light Primrose Yellow, near 4C, surrounding a basal area a bit darker, near 144D. All these petals usually had a thin line along the petal margins of near 50A, Claret Rose, and sometimes with thin blushed streaks of a Delft Rose, near 46D and/or a Turkey Red, near 46C where the petals were first exposed to the sun. There were other buds where off-white, near 159D from the Orange-White Group, was the only color seen, often with no noticeable blushing or streaking. These flowers opened a creamy white.

Bloom:

*Form.*—The upper profile of the individual blooms began flattened, became high centered and convex, and finished flattened convex as the flowers faded. Lower profiles began cupped, gradually became flattened concave in the full open bloom, and finished quite concave as the petals drooped and faded.

*Size.*—First blooms in the center of the first clusters on any cane were largest, opening to a diameter of $3^{13}/_{32}$ to $3^{23}/_{32}$ inches. When fully expanded, remaining flowers in the cluster and those on subsequent flowering stems were somewhat smaller with diameters varying from as small as $2^{8}/_{32}$ inches to as large as $3^{2}/_{32}$ inches and with depths of $1^{4}/_{32}$ inches to $1^{21}/_{32}$ to inches.

*Lasting quality on plant.*—From sepals closed to full open bloom was 8 to 9 days. Blooms remained fresh, on average, for an additional 7 to 8 days.

*Fragrance.*—None to mild and sweet.

*Petalage.*—20 to 35 with the highest petal count noted in mid summer.

*Petaloids.*—12 to 20. While most originated inside the inner the petals, a few were interspersed between the inner and intermediate petals.

Petals:

*Arrangement*.—Imbricated.

*Persistence*.—Marcescent; after they withered, the petals were slow to drop or did not drop until after hips started to form. Often they remained permanently attached to their receptacles, which also did not drop but remained firmly attached to the peduncles, long after they withered.

*Thickness*.—Moderately thick.

*Substance*.—Excellent.

*Texture*.—Adaxial and abaxial surfaces were both satiny.

*Appearance*.—On the adaxial surfaces all veins were slightly recessed. The abaxial surfaces had only main veins protruding somewhat, and those were visibly fanning out from the basal area.

*Form*.—Broadly oblate.

*Outer margins*.—Crescent.

*Apex*.—Retuse; occasionally with two rounded notches on either side of a rounded apex.

*Base of petals*.—Curvilinear.

*Size outer petals*.—Outermost petals varied from 1 12/32 to 2 2/32 inches wide. Heights of petals varied from 1 4/32 to 1 23/32 inches from the points of attachment to the outer margins, and with the distance from the points of attachment to the base of the notches at the apex usually 1/32 to 2/32 inch shorter.

*Color*.—Most flowers were a combination of cream-white and varying pinks from the moment the sepals divided, while some opened only a near white color. When full open, all flowers appeared the same in all aspects, including color, regardless of their color when the petals first unfurled.

*Color of flowers that opened predominately pink with creamy white, as viewed in patent image* 1-2.—(1) When the sepals first divided in the spring, the colors seen on some petals were a light Chartreuse Green, near 1C, surrounding a basal area of a darker yellow green, near 145B, and on other petals, a very light Primrose Yellow, between 4C and 4d, surrounding a basal area a bit darker, near 144D. Both color combinations appeared on the same bud. Visible petal margins had thin edges of a deep Claret Rose, near 50A. When light exposure was more intense, there were streaks of a Delft Rose, near 46D, and/or a Turkey Red, near 46C. (2) When the flowers had opened to exhibition stage (somewhat less than half open), the adaxial surfaces of the OUTER PETALS were a cream-white, between 11D and 155B, suffused with medium shades of Neyron Rose, near 55B, and with darker streaks near 55A, throughout. The Basal areas were near very light yellow-green, near 145D, and the points of attachment, were a darker yellow-green, between 145A and 144D. The abaxial surfaces were between 159D and 155B with the blush from the upper surface showing through as a pale pink between 62D and 49D. The basal areas were near 145D and the points of attachment were near 145B. INTERMEDIATE PETALS had adaxial surfaces of near 55C, suffused with near 55B. The basal areas were a medium yellow near 3C. Points of attachment were a medium Mimosa Yellow, near 8B, or a medium yellow-green, near 145B, both colors frequently appearing on adjacent petals within the same flower. The abaxial surfaces were near 155B, with no hint of pink. Their basal areas were a Mimosa Yellow near 8B. The points of attachment were near 8B, or a medium green-yellow near 144C, relative to the color of the immediate adaxial surface. At this exhibition stage, INNER PETALS were still curled into the center of the flowers and therefore had not been exposed to sunlight. Their adaxial surfaces were a combination of white, near 155B, and a very pale pink near 56D, and with more of the petal lightly suffused with near 55B. The basal areas were near 8C, becoming near 8D near the points of attachment. Points of attachment were either near 8D or near 1A, a very light chartreuse green. The abaxial surfaces were near 155B with the pink of the upper surface showing through as near 56D. The basal areas were near 8D, and the points of attachment were near 8B. (3) Particularly in the spring, the yellow of the basal areas of some of these blooms appeared somewhat deeper in color and more prominent. The yellow accentuated the cream-white and pink, lending to the impression of vibrant pink, cream and yellow blend flowers. The yellow was not as noticeable on subsequent blooms.

*Colors of flowers that were predominantly near-white when they first opened, as viewed in patent image* 1-3.—(1) When Sepals first divided, the color seen was a white, near 159D from the Orange-White Group, and occasionally a small portion of a petal had a small streak of near 58A, Indian Lake, where light exposure had been strongest. (2) When sepals were down, adaxial surfaces were a white, between 158D and 155D. Abaxial surfaces of the petals were a soft creamy yellow, between 159B and 13D, and occasionally with the streak of near 58A, where the sepals had first divided. (3) When flowers were full open but petals were still turgid and fresh, the adaxial surfaces of the OUTER PETALS were a very pale creamy yellow between 19D and 11D, with a blush of near 55B, Neyron Rose, the deepest blush closest to the margins. The points of attachment were near 2D, a light chartreuse yellow. The abaxial surfaces were lighter, a creamy white between 11D and 155D, down to the points of attachment, which also were near 2D. INTERMEDIATE PETALS were varying shades of medium pink, between 49C and 55C, on the adaxial surfaces, except along the central veins where they were white, near 155D. Their basal areas and points of attachment were near 11D. The entirety of the abaxial surfaces was a pale cream-yellow between 11D and 155A, suffused with near 49D toward the upper and outer edges. The adaxial surfaces of the INNER PETALS AND PETALOIDS were a medium-light pink, between 36C and 49C, with basal areas and points of attachment, near 11D. The abaxial surfaces of the inner petals and petaloids were somewhat lighter, between 36D and 49D, and with basal areas and points of attachment near 11D. When full blown, the colors on all blooms, whether they opened pink and creamy white or just creamy white, appeared the same. Just before the petals began to lose turgidity, adaxial surfaces were between 11D and 155D, and the outer edges most exposed to the sun had varying amounts of blushing near 55B, and sometimes between 55A and 52C right along the margins. Abaxial surfaces also were between 11D and 155D with the flush from the upper surfaces showing through. Points of attachment were near 2D. As the blooms continued to age, the intensity of the pink blushing continued to increase and became deeper in color.

Petaloids:

*Texture and color*.—Were the same as that of the adjacent petals.

*Unique characteristics*.—Petaloids were smaller and of different forms than the petals. Margins were often ruffled. Petaloids interspersed between petals were usually cordate, attached to the receptacle on a narrow, elongated base. Closer to the center of the flower, petaloids were often oval shaped, being taller than wide, in contrast to the petals that were wider than tall. Bases were usually oblique and were attached to the receptacle by filaments. These inner petaloids were sometimes curled, folded over or wrapped around each other; some had one margin running along the central vein; some were bifid; occasionally there was a sterile anther attached or the petaloid was wrapped around an anther. Those that were bifid had a streak of near 155D from the points of attachment to the points of divide along the margin.

*Size*.—Petaloids were measured up to 1 12/32 inches wide and 1 14/32 inches long and down to as small as 4/32 inch wide by 7/32 inch long.

General tonality: This new rose plant has flowers of varying shades of light and medium pinks and creamy white blends. In the spring in particular, the medium yellow from the base of the petals of a number of the blooms became quite evident causing the flowers to appear a vibrant pink, cream and yellow blend.

Sepals: Rolled back ahead of the petals. They were permanently attached to the receptacle.

*Shape*.—Outer sepals were elliptical with truncated bases and lanceolate apices. Inner sepals were oblong-ovate with truncated bases and linear apices.

*Margins*.—Outer sepals were edged with stipitate glands and fine hairs. Along each margin were two lanceolate foliar appendages that were also edged with stipitate glands. Inner sepals were only edged with fine hairs.

*Appearance*.—Outer surfaces of the outer sepals were covered with fine hairs; toward the margins were two rows of stipitate glands, near parallel to the stipitate glands on the margins. Outer surfaces of the inner sepals had many single hairs in the center; hairs became heavy and appressed toward and along the margins. Inner surfaces of all sepals had a vestiture of appressed tomentum.

*Color*.—The outer surfaces were near 137B with a lighter basal area and some blending in randomly either side of the central vein of near 144A. There were streaks and small blotches flushed with near 183B, from the Greyed-Purple Group. With direct light exposure, they were completely flushed with near 183A, heaviest down the middle, and with streaks of near 183B throughout. Stipitate glands were tipped either near 183A or near 183B. Inside surfaces were near 137C; the basal area and main vein up through the middle were lighter, near 145C. The tips of the apices were flushed between 183A and 183B.

*Size*.—Widths of the sepals on full open flowers were measured from 10/32 to 14/32 inch. The lengths of the sepals varied from 28/32 inch to 1 12/32 inches.

Peduncles: Usually remained firmly attached to the stem until well after they had dried and shriveled and the flowers from further down the cane had also opened and dried.

*Aspect*.—Erect, often with a slight curve just below the receptacle.

*Strength*.—Strong.

*Color*.—Near 144A, Lettuce Green. Anthocyanin coloration was variable: It may be completely absent; it may be weak on one side and absent on the other; or it may be weak on one side and strong on the other, relative to the amount of direct light it received. When present the color ranged between 180A and 181B, from the Greyed-Red Group. This is visible in the patent images: Patent Image 2-1 was a plant growing in full sun in California and has the darkest anthocyanin coloration; the plants in Patent Images 1-2 and 1-3 received a moderate amount of sun and the plant in Patent Image 1-1 received the least amount of sun and is displaying no anthocyanin coloration.

*Texture*.—Semi-glossy.

*Appearance*.—There were random single hairs and numerous stipitate glands their entire length of the peduncle. The stipes, themselves, were near 145D and the glands were colors varying from 175D to 175A from the Greyed-Orange Group. A few prickles were found on some peduncles that were near 175A.

*Size*.—Diameters of the peduncles were uniformly 4/32 inches. (1) Each peduncle was attached to its own flowering stem. Within each cluster, the flowering stems varied greatly but were usually short. Lengths of the peduncles also varied greatly within the cluster as shown in Table 2.

TABLE 2

| PEDUNCLE | 1ST CLUSTER | 2ND CLUSTER ON THAT CANE |
|---|---|---|
| To main bud | 2 12/32 inches on a 21 1/4-inch flowering cane. | 1 30/32 inches on a 8 5/8-inch flowering stem |
| To 2nd bud | 2 6/32 inches on a 14/32-inch flowering stem. | 1 19/32 inches on a 8/32-inch flowering stem |
| To 3rd bud | 1 29/32 inches on a 9/32-inch flowering stem | 30/32 inch on a 7/32-inch flowering stem |
| To 4th bud | | 1 4/32 inches on a 10/32-inch flowering stem |
| To 5th bud | | 1 22/32 inches on a 11/32-inch flowering stem |

(2) Lengths varied by the stage of the flower. In table 2, the flowers were in bud stage, with sepals closed or just starting to crack open. Table 3 compares a cluster at bud stage to 2 weeks later when the main bud had opened and was beginning to fade, buds 2, 4 and 5 were half open at exhibition stage, and bud 3 had the sepals just starting to unfurl.

TABLE 3

How the peduncles grew.

| PEDUNCLE | MEASURED Jun. 26, 2012 | MEASURED Jul. 8, 2012 |
|---|---|---|
| To main bud | 1 30/32 inches | 1 30/32 inches |
| To 2nd bud | 1 19/32 inches | 1 28/32 inches |

TABLE 3-continued

How the peduncles grew.

| PEDUNCLE | MEASURED Jun. 26, 2012 | MEASURED Jul. 8, 2012 |
|---|---|---|
| To 3rd bud | 30/32 inch | 1 14/32 inch |
| To 4th bud | 1 4/32 inches | 1 10/32 inches |
| To 5th bud | 1 22/32 inches | 2 2/32 inches |

Receptacle: Chalice-shaped.

*Size*.—Diameters were 11/32 to 13/32 inch in bud stage to 16/32 to 20/32 inch with blooms full open. At bud stage, the heights were noted to be the same as the diameter. When blooms were full open, the height noted was 2/32 inch greater than the diameter.

*Color*.—When grown where light was most intense, the color was near 144A, Lettuce Green. There was a heavy blush adjacent to the corolla of near 180B, a medium shade from the Greyed-Red Group, and with a lesser degree of blushing progressing down the receptacle. When farther from, or somewhat protected from, the light source the color became lighter, being shades between 144B and 143C. When as light as near 143C, there was usually no anthocyanin blush.

*Appearance*.—Glossy and glabrous.

*Texture*.—Occasionally there were random hairs near the base.

REPRODUCTIVE ORGANS

Stamens, filaments and anthers:

*Quantity*.—Varied from 176 to 184 or more.

*Arrangement*.—A row of the tallest stamens was located just inside the corolla; a second row, a bit shorter, was located immediately inside and adjacent to the first row; then a third row of stamens of mixed lengths was located immediately inside and adjacent to that second row; and finally, a partial row of the shortest stamens was located immediately inside and adjacent to the third row.

*Filaments*.—Their color was near 16C, a Buttercup Yellow. The longest filaments were measured from 15/32 to 16/32 inch, those in the next row in were measured from 11/32 to 12/32 inch, and the shortest ones and those of mixed lengths were measured from 3/32 to 8/32 inch.

*Anthers*.—Their color was the same as the filaments, near 16C. They were measured 3/32 inch long and 2/32 inch wide.

*Pollen*.—There was an ample amount of pollen, near 23A, Cadmium Orange.

Pistils, styles and stigmas:

*Quantity*.—Was around 98.

*Arrangement*.—The pistils originated in an alveola in the center of the top of the receptacle.

*Styles*.—All were thin. Some were very straight, some were gently undulate and some only had a gentle curve near the top. Lengths varied from 3/32 to 11/32 inch. Color of some was a medium color from the Greyed-Orange Group, near 165C, and some were a medium color from the Greyed-Purple Group, near 186A, and within the same flower.

*Stigmas*.—Colors of some of the stigmas were near the same as the styles to which they were attached. Most stigmas attached to styles of near 186A were also near 186A. Other stigmas were near 163C, a straw-yellow from the Greyed-Orange Group, and were usually attached to styles of near 165C. Stigmas measured 2/32 inch long.

Hips: There were three hips available to observe.

*Size*.—The diameter of two was 1 2/32 inches with heights of 24/32 and 25/32 inch. The third hip had a diameter of 31/32 inch and a height of 21/32 inch.

*Surface*.—The appearance was semi-glossy and glabrous. There were occasional hairs scattered on the surface, increasing somewhat in quantity at the bottom nearing the peduncle and at the top nearing the sepals.

*Color*.—When mature colors on areas most directly exposed to the sun were 171B and 171A, a rust orange from the Greyed-Orange Group, and on adjacent areas with less sun exposure near 163B, a golden-straw color also from the Greyed-Orange Group. Areas away from the sun were a Scheele's Green, near 143C.

PLANT

Habit: Upright, uniformly branched.

Growth: Vigorous and hardy: On mature plants, the first cluster on a cane began with three to six buds. The central bud usually appeared recessed to varying degrees within the cluster as the other flowering shoots grew up and often became taller than the central bud they surrounded. Additional flowering shoots developed progressively, from each node on the cane below the cluster, well before the buds in the cluster started to expand, and quickly grew up to, or occasionally exceeding, the height of the original cluster. Each flowering shoot developed its own cluster of 2 to 6 buds. All these flowering stems originating on a single cane comprised the spray, having 30 to 40 or more buds and flowers in color simultaneously. Younger plants often only had 10 to 16 buds in a spray, as the subordinate flowering shoots comprising the spray occasionally had small clusters but mostly bore only a single bloom.

*Size*.—The observed plants grew 25 to 33 inches tall in one year.

*Root initiation from cuttings*. Under controlled greenhouse conditions, was 4 to 5 days.

*Length of flowering stems*.—The first canes in the spring were 18½ to 28½ inches long and initially terminated in a single bloom. (1) The buds that developed from the base of and/or just below the base of the peduncle of that first flower forming the cluster, had short flowering stems of their own, connecting their peduncles to this main flowering cane. They were measured as short as 8/32 inch and as long as 1 3/32 inches. (2) Flowering stems continued to develop from the nodes below the first cluster, as depicted in Patent Image 1-1. They varied in length according to the distance from the crown of the plant. Some were measured with lengths from 5½ inches up to 11⅜ inches, in consecutive order, from top to bottom, forming a spray around the cluster at the top. (3) Each flowering stem would usually end in a cluster of 2 to 5 flowers. The flowering stems within these clusters were longer than the flowering stems in the first cluster at the top of the main cane. They were measured 1 30/32 to 4 inches long. (4) Flowering stems would also develop from the nodes of the flowering stems in paragraph (2). They varied in lengths according to the distance to the outer circumference of the plant, rather than to the crown, and often terminated with a single bloom, especially on younger plants. These were measured at lengths from 4⅛ inches to 10½ inches.

Foliage: Pinnately compound, most often with 5 leaflets but also with 3, 6 or 7. The three-leaflet leaves were mostly located at the top and base of each flowering stem. Six- and seven-leaflet leaves, when present, were located on the lower third of the flowering stems.

*Size of mature leaves*.—Averaged 5⅞ inches for the five-leaflet leaves. Six and seven-leaflet leaves averaged ¾ inch shorter.

*Leaflets*.—Shape was broad ovate. Their bases were rounded and obtuse. Apices were cuspidate.

*Appearance*.—The adaxial surfaces were notably glossy when young and became more near semi-glossy when old. Veins were deeply recessed. The abaxial surfaces were matte. Main veins protruded completely; primary lateral veins protruded near completely. There were two to five prickles along the main veins where they first entered into the terminal leaflets and the uppermost pairs of leaflets. They decreased in size as they progressed into the leaflet.

*Texture*.—The adaxial surfaces were glabrous. The abaxial surfaces were leathery.

*Edge/margin*.—Serration was simple and fine. There were glands on the tip of each serrate with stipitate glands along the basal margin, and some between the serrates along the basal margin.

*Color new foliage*.—Adaxial surfaces were a medium green between 144A and 143C, and flushed with near 183A, from the Greyed-Red Group, heaviest along the margin and the along the veins. The veins retained their deep coloration, well after the flush began to fade from the rest of the leaflet. The abaxial surfaces were nearest 144B, a Scheele's Green, and flushed with near 183B, Oxblood Red, heaviest along the margins.

*Color older foliage*.—The adaxial surfaces first became near 137A, and finally became a very dark green between 139A and 147A. The medium green on abaxial surfaces first became between 137C and 147C, and finally became between 137C and 147B. Only the oldest foliage was lacking any anthocyanin coloration.

*Petioles*.—Color on the adaxial surfaces on young foliage appeared near 183C, and between the stipules it was lighter, near 182C. The abaxial surfaces were completely flushed with a Greyed-Orange, between 177C and 176C. When old, the ridges along the adaxial surfaces were the same dark green color as the adjacent leaf surfaces. The color in the grooves became near 146A and between the stipules it was near 144A. The abaxial surface became near 144B. SIZE OF PETIOLES: Petioles were measured from as short as 30/32 inch to as long as 1 30/32 inches, with the shorter petioles on the shorter leaves. Girths varied from 2/32 to 4/32 inch, regardless of the leaf size. TEXTURE OF THE PETIOLES: Along the ridges on the adaxial side there were numerous stipitate glands. The grooves had many single hairs. The abaxial surface had one to three prickles in a line along center and many stipitate glands along the sides.

*The rachis and petiolules*.—Were the same color and had the same texture as the petiole. On the abaxial surface of the mature leaf, the near 144B on its petiolules continued along the main vein going into its leaflets. SIZE OF RACHIS and PETIOLULES: The rachis varied in length from 28/32 inch to 1 16/32 inch, not relative to leaf size. They had a girth most often of 5/64 inch, varying from 2/64 to 5/64 inch. Petiolules to terminal leaflets were most often 20/32 inch long, varying from 15/32 to 24/32 inch and with a girth usually of 2/32 inch. TEXTURE OF THE RACHIS and PETIOLULES: There were two to three prickles in a line along the center of the abaxial side of the rachis, and two to four smaller prickles gathered along the sides just below the juncture with the outermost pair of leaflets. Petiolules usually had a single prickle on the abaxial surface.

*Stipules*.—Were paired at the base of each petiole. SIZE OF STIPULES: Lengths varied from 15/32 to 23/32 inch attached, not relative to leaf length, and from 4/32 to 13/32 inch angled out, not relative to stipule length, at about a 45° angle from the petiole. STIPULE MARGINS were loosely serrated and with many glands and stipitate glands along the entire margin. Margins of the part angled outward were not serrated but did have near evenly spaced stipitate glands. Edges rolled back. COLORS OF STIPULES were a medium green, between 137C and 146B, on the adaxial surface, and lighter, between 146B and 143C, on the abaxial surface.

Resistance: The plants growing in CA showed well above average resistance to both downy mildew and powdery mildew, as well as rust, and somewhat above average resistance to blackspot. The plants observed in MA demonstrated well above average resistance to blackspot and powdery mildew. Downey mildew and rust are not prevalent in MA.

Wood:

*Cane diameters*.—The diameter of main canes varied from 19/32 to 21/32 inch. Primary flowering stems had diameters varying from 9/32 to 11/32 inch. Secondary flowering stems had diameters ranging from 5/32 inch to 8/32 inch.

*Length of flowering stems*.—Depended on the distance to the crown or outer circumference of the plant. Main flowering canes were measured from 18½ to 28½ inches long. Secondary flowering stems, originating from those main flowering canes, were measured from 5½ to 11⅜ inches long. Tertiary flowering stems, originating from those stems, were measured 4⅞ to 10½ inches long. NODES were randomly spaced on all stems at 1 to 2⅝ inches.

*Color new wood*.—Was a medium green, between 146A and 137C.

*Color of old wood*.—As the stems matured they became a darker, bluer green, near 137A, flushed on one side in varying intensities with a brownish purple, between 200C and 183A. The oldest wood was a medium dark-green, between 146A and 147A, with anthocyanin coloration only absent from the oldest canes.

*Texture*.—New wood was glabrous. Old wood was glabrous with a few small spots where lenticels had begun forming near the bases of the canes. Lenticels were a medium Greyed-Brown near 199D.

Prickles: The FORM of the prickles was deltoid. The upper profile was usually slightly angled downward. The lower profile was often slightly concave.

*Quantity*.—On main flowering stems one to three prickles were located immediately below each node, with a total of three to five between nodes, regardless of the distance between the nodes. There were 10 to 20 in six inches of stem length with the larger quantity being on the oldest canes. On secondary flowering stems there were only the one to three prickles located immediately below each node.

*Size*.—On the main canes the prickles varied greatly in size from 8/32 to 19/32 inch long. On secondary and tertiary stems the prickles were 5/32 to 8/32 inch long. The lengths of all bases were about 1/32 inch longer than the prickles.

*Color*.—When young, prickles were a medium color from the Greyed-Red Group, near 182B. When older, the prickles were a dark brown, near 200A. When very old they lightened to near 199B, sometimes with streaks of the near 200A, and bases had become near 199C.

The new invention claimed is:

1. A new and distinct variety of hardy rose plant of the floribunda class, substantially as illustrated and described herein.

* * * * *

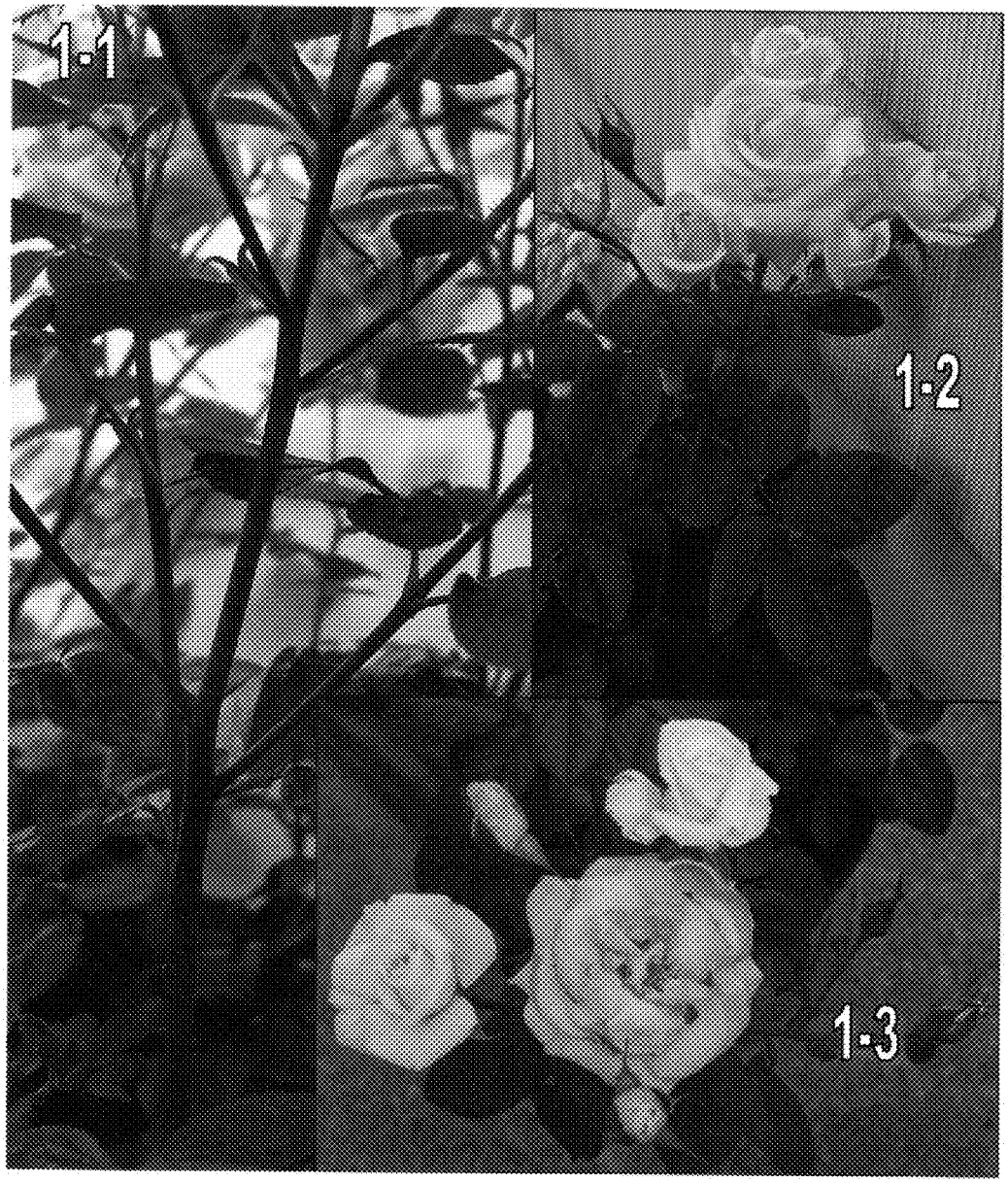
1-1
1-2
1-3

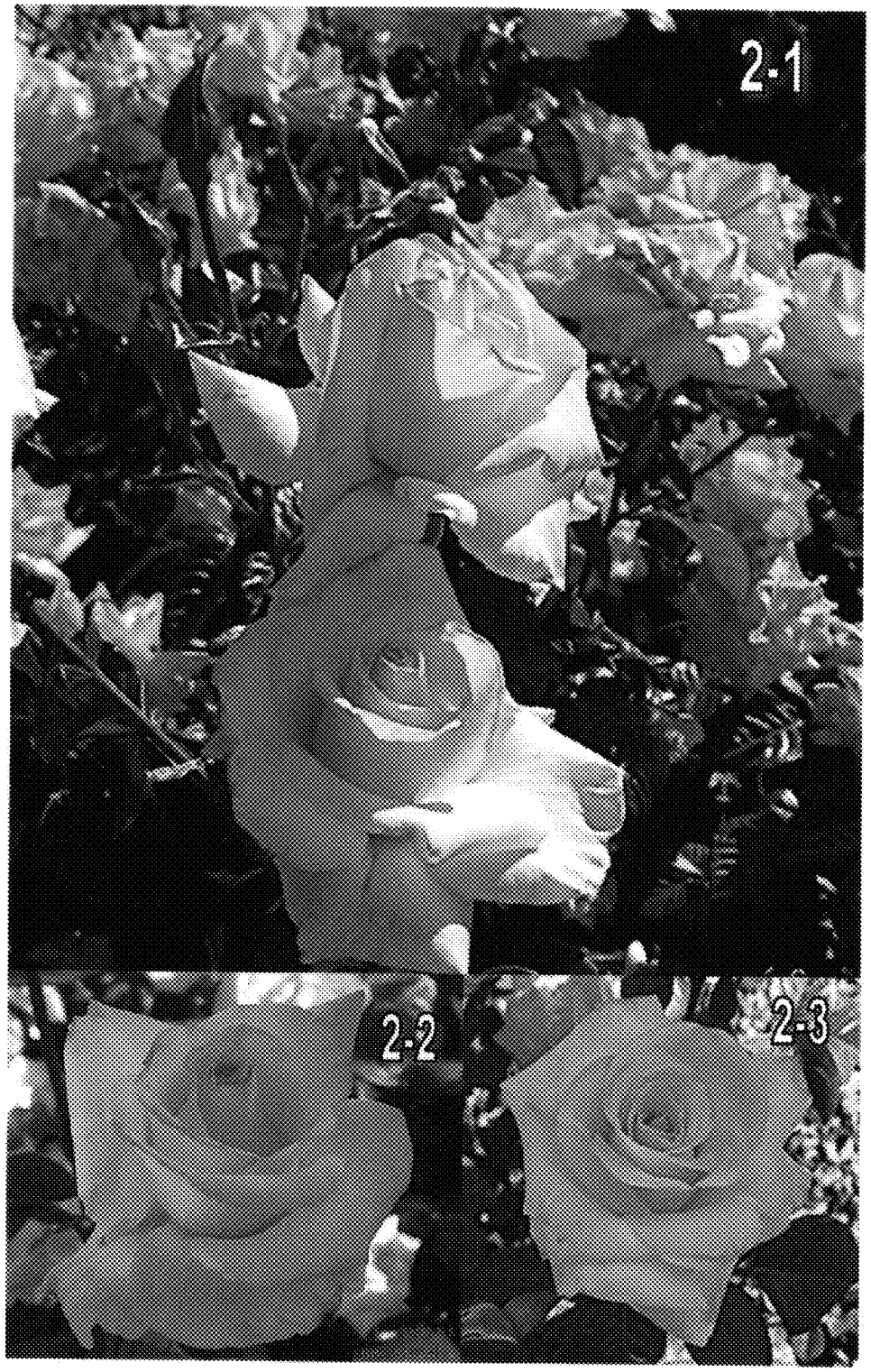
2-1
2-2
2-3